United States Patent [19]
Adachi

[11] Patent Number: 5,674,183
[45] Date of Patent: Oct. 7, 1997

[54] FIBERSCOPES AND SPRAY MODULES

[75] Inventor: Saburo Adachi, Osaka, Japan

[73] Assignee: Adachi Company, Osaka, Japan

[21] Appl. No.: 577,668

[22] Filed: Dec. 22, 1995

[30] Foreign Application Priority Data

Dec. 26, 1994 [JP] Japan ................. 6-338113

[51] Int. Cl.[6] ........................................ A61B 1/12
[52] U.S. Cl. ........................ 600/158; 600/156; 600/159
[58] Field of Search ........................ 600/105, 135,
600/153, 154, 155, 156, 157, 158, 159;
606/119, 191, 193; 285/175, 176; 251/12,
227, 341, 349, 339

[56] References Cited

U.S. PATENT DOCUMENTS

| | | | |
|---|---|---|---|
| 4,258,721 | 3/1981 | Parent et al. | 600/158 |
| 4,924,851 | 5/1990 | Ognier et al. | 600/158 X |
| 5,447,148 | 9/1995 | Oneda et al. | 600/158 X |

FOREIGN PATENT DOCUMENTS

| | | | |
|---|---|---|---|
| 4-336027 | 11/1992 | Japan | 600/156 |
| 2 014 455 | 8/1979 | United Kingdom . | |

*Primary Examiner*—Beverly M. Flanagan
*Attorney, Agent, or Firm*—Cushman Darby & Cushman IP Group of Pillsbury Madison & Sutro, LLP

[57] ABSTRACT

A fiberscope comprises an elongated flexible tubular member having an axially extending channel, an operator unit 2 for performing an endoscopic observation or treatment through the channel, a mounting recess 21 formed in the operator unit, an adapter 8 which can be mounted in the mounting recess, and a spray module 7 having a spray nozzle 33 which can be connected to the adapter 8. As the spray module 7 is pressed to the adapter 8, the valve mechanism of the spray module 7 is opened so that a compressed gas is ejected from the tip of the tubular member through the bore 42 of the adapter 8 and the gas passageway 23 in the operator unit 2, and, thus, deposits on the open end of its internal channel are removed with jets of a gas.

15 Claims, 6 Drawing Sheets

FIBERSCOPES AND SPRAY MODULES

FIELD OF THE INVENTION

This invention relates to a fiberscope for use in the endoscopic observation and/or treatment of lesions, for example in the digestive organs of the man or animals, and a maintenance spray module which is useful for removing deposits from the nozzle or open end of a flexible tubular member of the fiberscope.

BACKGROUND OF THE INVENTION

The fiberscope generally comprises an elongated flexible tubular member having an internal channel extending axially therethrough and an operator unit, which is attached to the tubular member, for endoscopy and treatment of lesions through the channel. The internal channel of the tubular member comprises channels for an optical fiber (fiberoptic bundle), air and water, aspiration, and biopsy and foreign-body forceps, among others.

In the observation or treatment within the stomach, for instance, by flexible endoscopy, body fluids such as blood, gastric juice, and mucous secretions as well as proteins invade the open end (nozzle end) of the air-water channel to form deposits at and around the nozzle end to ultimately plug the nozzle and render it inoperable. Therefore, it is common practice to hung the fiberscope after use to let the tubular member droop down so that the adherent body fluids and the like may drip out spontaneously.

However, this drainage practice is not only timeconsuming but does not insure complete removal of the body fluids and the like. Moreover, since portions of deposits of the body fluids remain within the nozzle end and get coagulated in situ, smooth communication can hardly be maintained in the air-water channel. It is possible to remove coagulated deposits with a fine needle or the like inserted into the open end of the air-water channel but since the channel is as small as about 0.1 to 0.3 mm in diameter, it is not only difficult to remove the coagulated deposits but the tip of the needle may injure the internal wall defining the channel. Moreover, once the channel is injured, a costly nozzle piece such as a distal end for the air-water channel must be substituted with a new one.

On the other hand, it might be contemplated to remove deposits from the nozzle end of the air-water channel by inserting a nozzle of a spray module filled with a pressurized gas into the other open end of the air-water channel which is opposite to the nozzle end and ejecting the compressed gas from the nozzle end. However, one end (nozzle end) of the air-water channel is situated at the tip of the tubular member while the other end (where the spray nozzle is inserted) is situated at the end of the tubular light guide member extending out from the operator unit. The light guide member has a light guide and an air-water passageway. Moreover, the operator unit is formed with an opening which, upon closure, communicates the air-water passageway in the light guide member with the air-water channel in the tubular member. Therefore, in order to remove deposits on the nozzle end, it is necessary to simultaneously establish an operation for communicating the air-water passageway in the light guide member with the air-water channel in the tubular member by obstructing the opening (hole) of the operator unit and an operation inserting the insertion part of the light guide member into the nozzle of the spray module and pressing of the spray module against the operator unit. These operations require two persons and the removal of deposits involves a tedious procedure.

To overcome these disadvantages, the inventor of this invention previously proposed a fiberscope spray module comprising a spray nozzle or auxiliary nozzle for fitting the air-water supply port to the module filled with pressurized gas and an insert guide for accepting the light guide of a fiberscope as disposed in association with the air-water supply port (Japanese Utility Model Publication No. 40250/1991 (JP- Y2-3-40250 and Japanese Utility Model Publication No. 41682/1991 (JP-Y2-3-41682)). With this spray module, the compressed gas in the spray module can be fed to the air-water passageway by the simple procedure of closing up the opening of the operator unit which is communicating with the air-water passageway for preventing leakage from the opening (hole) and depressing the end of the light guide to press the spray nozzle. Therefore, the body fluid and other deposits at the open end of the air-water channel of the fiberscope can be removed by a single person without damaging the channel.

However, when the above spray module is used, the end of the light guide is situated in a position remote from the fiberscope operator unit. Therefore, in order that the compressed gas in the module may be ejected from the open end of the air-water channel of the tubular member of the fiberscope, it is necessary to close up the opening by one hand and depress the end of the light guide inwardly with respect to the spray module by the other hand. Thus, both hands must be used to remove the deposits so that the system was not satisfactory enough in manipulatability.

Such problem also occurs in a case that scale is deposited or accumulated on the open end of the air-water channel when water, particularly hard water, is supplied from the light guide unit through the air-water passageway to the air-water channel for washing a lens mounted on the tip of the optical fiber.

SUMMARY OF THE INVENTION

It is, therefore, an object of this invention to provide a fiberscope spray module with which the deposits at the open end (nozzle end) of the channel of a tubular member can be removed positively and in a simple manner.

It is a further object of the invention to provide a fiberscope spray module such that deposits at the open end (nozzle end) of the air-water channel of the tubular member can be efficiently removed simply by pressing a compressed gas supply means and an operator means against each other.

It is a still another object of this invention to provide a fiberscope and a spray module with which the deposits at the open end (nozzle end) of the air-water channel of the tubular member can be removed easily by one hand.

After intensive researches were done to accomplish the above-mentioned objects, the inventor of this invention found that when a compressed gas supply means for supplying a compressed gas to the channel of the elongated flexible tubular member is removably connected to the operator unit of a fiberscope for performing an endoscopic observation or treatment, the deposits at the tip of the tube can be easily removed by single-handed operation. This invention has been developed on the basis of the above finding.

Thus, the fiberscope of this invention comprises an elongated flexible tubular member having an axially extending channel and an operator means connected to the tubular member and adapted to perform an endoscopic observation or treatment, the operator means is provided with a mounting means by which the compressed gas supply means for supplying a compressed gas can be detachably connected to the channel.

The above-mentioned mounting means comprises an adapter which can be connected to the compressed gas supply means and a mounting part formed in the operator means and adapted to accept the attachment of the adapter. The adapter may be formed with a bore communicable with the compressed gas supply means and the operator means may be formed with a fluid passageway communicable with the bore of the adapter and the channel of the tubular member. The adapter need only be interposed between the compressed gas supply means and the operator means. Thus, the adapter may be secured either to the mounting part of the operator means or to the compressed gas supply means. The compressed gas supply means may be any means that is capable of causing a fluid to be ejected into the channel of the tubular member and it is generally a spray module filled with a pressurized gas.

The spray module for maintaining a fiberscope of the present invention is useful for removing the deposits at the tip of the tubular member of a fiberscope with a jet of fluid for cleaning the tip of the tubular member. This spray module comprises a pressure-resistant container filled with a compressed gas, a spray nozzle which is capable of advancing inward with respect to the pressure-resistant container, a valve mechanism for ejecting the compressed gas in the pressure-resistant container from the spray nozzle in association with the inward movement of the spray nozzle, and an adapter which can be connected to the operator unit for the tubular member of a fiberscope. The above-mentioned adapter is provided with a bore for communicating the spray nozzle with the channel in the tubular member through a fluid passageway formed in said operator means. The fluid passageway may comprise a gas (air) sub-passageway, a water sub-passageway or the both sub-passageways.

In the fiberscope of this invention, a compressed gas supply means is connected to the mounting means of an operator means, whereby the gas is fed to the air-water channel in the tubular member and ejected from the open end (nozzle) of the channel. Unlike the conventional system, the air-water passageway extending along the light guide from the operator means and the air-water channel extending from the operator means to the nozzle end need not be brought into communication by closing operation for closing up the opening of the operator means. Rather, by the simple procedure of feeding a compressed gas from the compressed gas supply means attached to the mounting means, the body fluid and other matter remaining adhered in and around the open end can be removed with certainty.

Moreover, since the compressed gas supply means can be freely connected and disconnected with respect to the mounting means, the fiberscope not provided with the compressed gas supply means can be used for the observation and treatment of the gastrointestinal tract or other organ. On the other hand, when the body fluid and other matter deposited on the open end of the channel of the fiberscope tubular member is to be removed, the compressed gas supply means is attached to the mounting means to remove the deposited matter.

According to the spray module of this invention, when a spray nozzle piece is forced into a pressure-resistant container, a valve mechanism is actuated so that the compressed gas within the pressure-resistant container is ejected from the spray nozzle. Meanwhile, by means of the bore of an adapter which can be attached to the operator means, the spray nozzle and the channel of the tubular member are brought into communication through the fluid passageway in the operator means so that the compressed gas from the spray nozzle flows to the channel and is ejected from the open end of the channel.

With the fiberscope and spray module of this invention, the deposits on and around the open ends of the air-water and other channels in the tubular member can be removed with high efficiency and certainty by letting a compressed gas flow out from the compressed gas supply means mounted in the mounting means. Moreover, by relative depressing operation of the compressed gas supply means comprising the spray module and the operator means, the deposits can be easily removed with certainty. Particularly because the compressed gas can be ejected by a single-handed operation, the plugging of the fine channels can be prevented with a simple operation for a long period of time.

DETAILED DESCRIPTION OF THE PREFERRED EMBODIMENT OF THE INVENTION

A preferred embodiment of this invention is now described with reference to the accompanying drawings.

Figure 1:
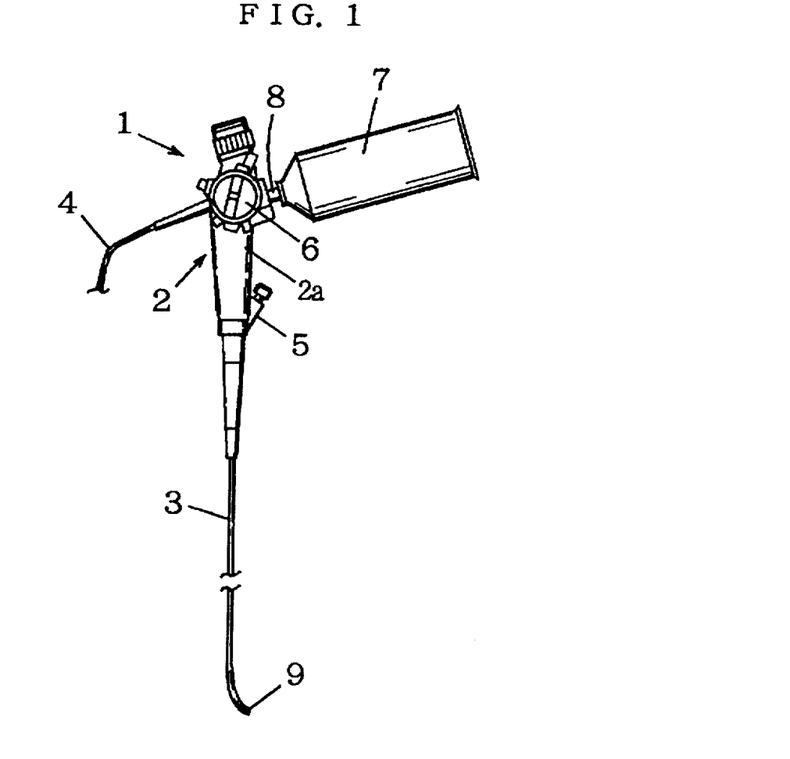
FIG. 1 is a schematic diagram showing the status of the fiberscope of the invention in use.
Figure 2:
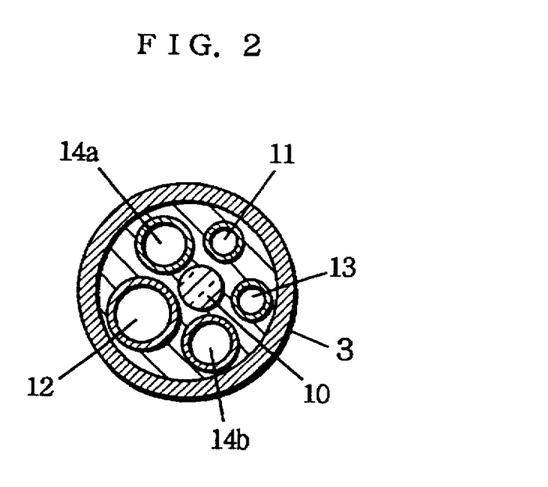
FIG. 2 is a sectional view of the tubular member of the fiberscope shown in FIG. 1.
Figure 3:
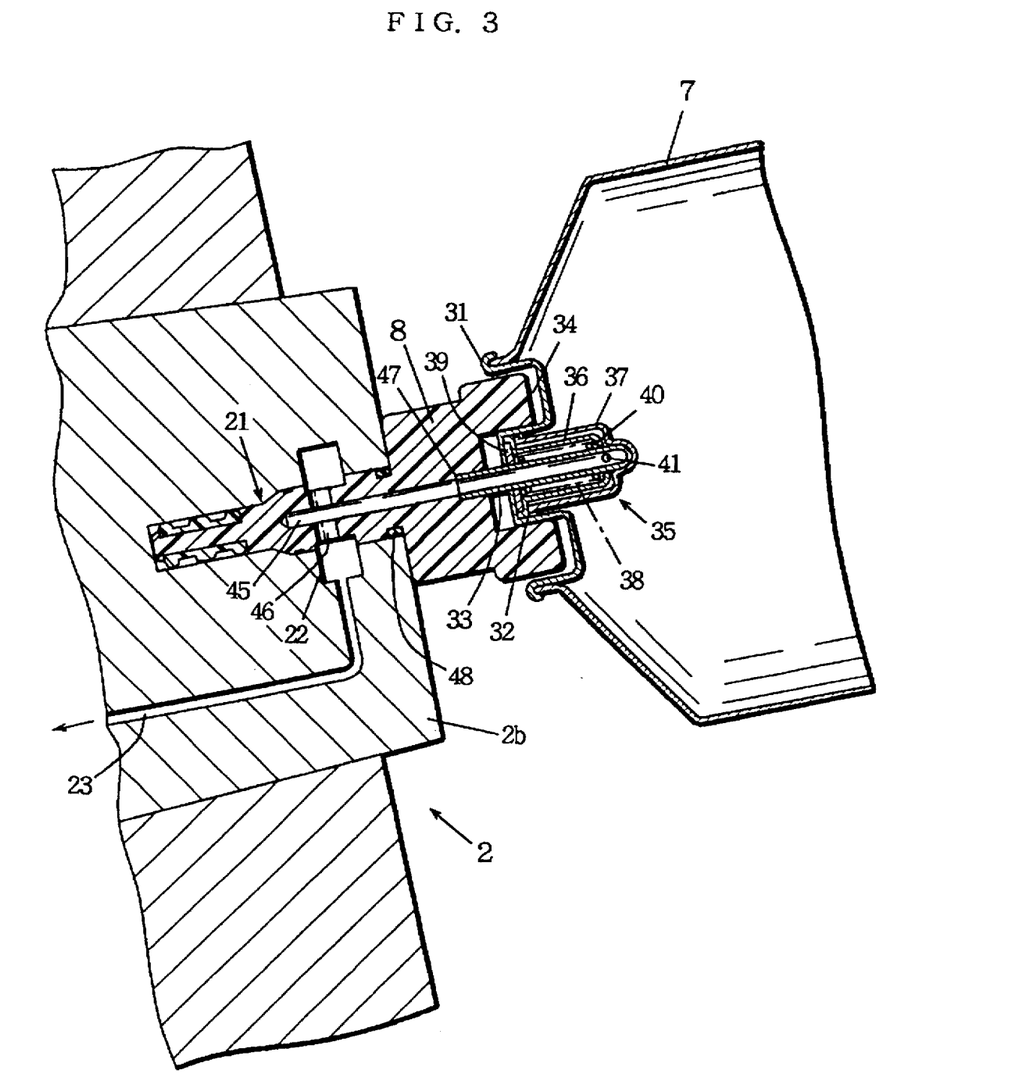
FIG. 3 is a sectional elevation view of the mounting mechanism in the operator means of the fiberscope as shown in FIG. 1.
Figure 4:
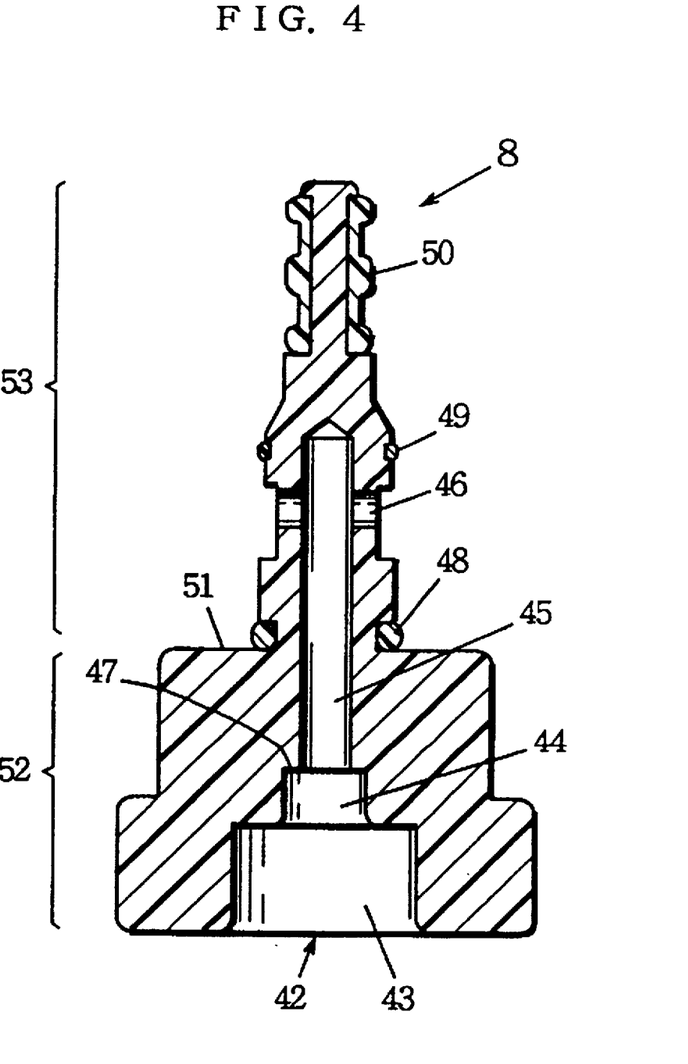
FIG. 4 is a sectional view of the adapter shown in FIG. 1.

FIGS. 1 to 4 illustrate an embodiment of a fiberscope according to the present invention. FIG. 1 is a schematic diagram showing the status of the fiberscope in use, FIG. 2 is a sectional view of the tubular member of the fiberscope, FIG. 3 is a sectional view showing the mounting mechanism of the operator means, and FIG. 4 is a sectional view of the adapter constituting the mounting means.

This fiberscope 1 comprises an elongated tubular member 3 having an axially extending channel and an operator unit 2 attached to the tubular member 3. As illustrated in FIG. 2, the tubular member 3 includes not only a channel for accommodating an optical fiber 10 but also a plurality of other channels, e.g. a channel 11 for air and water, a channel 12 for forceps, an aspiration channel 13, and other channels 14a, 14b and each of these channels 11 to 13, 14a and 14b terminates at the open end 9 of the tubular member 3.

As can be seen from FIG. 1, a light guide unit 4 for transmitting light to the optical fiber (fiberoptic bundle) 10 extends from the operator unit 2 provided with a grip portion 2a. This operator unit 2 is further provided with a manipulating or maneuver means 6 adapted to rotationally and otherwise control the orientation or direction of at least forward end portion of the flexible tubular member 3 for optimizing the performance of an endoscopic observation or treatment through the channels 11–13, 14a and 14b and a forceps inlet 5, formed at the grip portion 2a, for connection to a pipe extending from a forceps device. The light guide unit 4 mentioned above comprises a light guide and an air-water tube (not shown) having a passageway (line) communicating with the air-water channel 11 in the tubular member 3. Thus, extending from the operator unit 2 in one direction is the flexible tubular member 3 and in another direction is the light guide unit 4 in such a manner that the air-water channel 11 of the tubular member 3 can be communicated, at the operator unit 2, with the passageway in the airwater supply tube (not shown) of the light guide unit 4. It is to be understood that a fluid such as a gas and/or a liquid (e.g. water) can be supplied to the gastrointestinal canal from the air-water outlet at the end of the light guide unit 4 through the passageway of the air-water supply tube and the air-water channel 11 of the tubular member 3.

As shown in FIG. 3, the mounting part 2b of the operator unit 2 is formed with a mounting means in which a spray nozzle 33 of a spray module 7, as the compressed gas supply means, can be detachably mounted and a gas passageway 23 for feeding a compressed cleaning gas from the spray module 7 to the air-water channel 11 of the flexible tubular member 3. In this embodiment, the mounting means comprises a mounting recess 21 in the mounting part 2b of the operator unit 2 and an adapter 8 which can be detachably mounted in the mounting recess, and the spray module 7 can be detachably connected to the adapter 8.

The air-water channel 11 of the flexible tubular member 3 and the passageway of the air-water supply tube of the light guide unit 4 can be brought into communication through a bore 42 of the adapter and a gas passageway 23 of the mounting part 2b. Furthermore, in order to prevent inflow of the gas ejected from the spray nozzle 33 into the air-water supply tube of the light guide unit 4 and insure an effective supply of the ejected cleaning gas into the air-water channel 11 of the flexible tubular member 3, a check valve (not shown) as a regulating means is interposed in the passageway on the adapter 8 side of the airwater supply tube of the light guide unit 4.

Furthermore, a mounting recess 21 is formed in the position corresponding to the orifice of the conventional operator unit of the fiberscope through which the air-water supply tube of the light guide unit is communicated with the air-water channel of the flexible tubular member by closure.

To be specific, a mouthpiece 31 having a cylindrical portion 32 expanding inwardly in the form of a cap and a ring-shaped recess 34 formed around the cylindrical portion is attached to one end of the pressure-resistant container (container unit) of the spray module 7, and a cylindrical spray nozzle 33 is extending form the center of the cylindrical portion 32. The spray nozzle 33 is open at one end with the other end being closed and provided with an orifice 41, formed in the side wall toward the closed end, for guiding the compressed cleaning gas to the open end.

The spray nozzle 33 is disposed in such a manner that it can advance into the spray module 7 and the spray module 7 is provided with a valve mechanism so adapted that as the spray nozzle 33 advances deeper into the spray module 7, the compressed cleaning gas may be ejected from the spray nozzle 33. Thus, the spray module 7 is internally provided with the valve mechanism 35 which comprises a first cylindrical valve member 36 having a ring-shaped collar portion at one end, with the other end being formed with a through-hole for the spray nozzle 33 and a second cylindrical valve member 37 housing the first valve member 36 in an axially reciprocable manner and adapted to lock or support the spray nozzle 33 extending through the first cylindrical valve member 36 at the bottom thereof.

In this valve mechanism, one end of the second cylindrical valve member 37 may contact with the ring-shaped collar portion and the portion of the spray nozzle 33 between the inner wall of the cylindrical portion 32 and the collar portion of the first cylindrical valve member 36 is provided with a packing 39 for sealing off the part through which the cylindrical portion 32 is extending. The bottom of the first cylindrical valve member 36 is fitted with an O-ring 40 for sealing the part through which the spray nozzle 33 is extending. Furthermore, between the first cylindrical valve member 36 the spray nozzle 33, there is interposed a coil spring 38 for biasing the spray nozzle 33 axially outwardly.

When the valve mechanism is used, the end face of the second cylindrical valve member 37 is abutted against the ring-shaped collar portion of the first cylindrical valve member 36 by the biasing force of the coil spring 38. Therefore, when the spray nozzle 33 is pressed inwardly of the spray module 7 against the biasing force of the coil spring 38, the second cylindrical valve member 37 is shifted inwardly along with the spray nozzle 33 so that a fluid passageway is created between the ring-shaped collar portion of the first cylindrical valve member 36 and the end face of the second cylindrical valve member 37. As a consequence, the compressed cleaning gas in the module 7 flows through the fluid passageway and the orifice 41 into the cylindrical spray nozzle 33 and is ejected from the forward end opening of the spray nozzle 33. When the above pressure is released, the second cylindrical valve member 37 as well as the spray nozzle 33 is shifted axially outwardly by the biasing force of the spring 38 to bring the end of the second cylindrical valve member 37 into pressure-contact with the ring-shaped collar portion of the first cylindrical valve member 36 so that the ejection of compressed gas is terminated.

The compressed gas to be filled into the pressure-resistant container of the spray module 7 includes, but is not limited to, for example fluoro- or chlorofluoro-carbon gases, substitute fluoro- or chlorofluoro-carbon gases, nitrogen gas, and air. The module 7 may be filled with an aseptic or disinfect solution, a cleaning solution or the like together with the compressed gas.

The adapter 8 that may accept the attachment of the spray module 7 comprises, as illustrated in FIGS. 3 and 4, a large-diameter base 52 having a cylindrical portion slidable in the ring-shaped recess 34 of the mouthpiece 31 of the module 7 and a small-diameter mounting tip portion 53 extending out from the base 52. In order that the fluid ejected from the spray nozzle 33 may be guided to the gas passageway 23 in the mounting portion 2b, the adapter 8 is formed with a T-shaped bore (hole) 42 extending axially from the end face of the base 52 and opening at the side of the mounting tip portion 53. Thus, the bore 42 comprises a cavity 43 formed at the end of base 52 and accommodating partially the expanded cylindrical portion 32 of the spray module 7, a hole segment 44 having an internal wall 47 extending axially from the cavity 43 and contacting the end face of the spray nozzle 33 for restricting the outward movement of the spray nozzle 33, a passageway 45 extending axially from the hole segment to the center of a mounting tip portion 53 and having a circular sectional configuration smaller in diameter than the outer diameter of the spray nozzle 33 and a side hole 46 extending in both directions perpendicular to the extending direction of the passageway and opening at the side of the mounting tip portion 53. In this embodiment, the passageway 45 and side hole 46 constitute a gas passageway communicable with the compressed gas supply means. Such an adapter can be made of various materials which can be easily molded, for example, a synthetic resin.

When the adapter 8 is attached to the spray module 7, as shown in FIG. 3, a clearance is formed between the ring-shaped recess 34 of the mouthpiece 31 of the module 7 and the end face of the base 52 of the adapter 8 as well as between the expanded portion 32 of the module 7 and the wall surface of the mounting recess 43 of the base 52 so that the spray module 7 may be forced into the adapter 8. Thus, the dimension from the tip of the spray nozzle 33 of module 7 to the expanded portion 32 is greater than the depth of the hole 44 having an abutting internal wall in the spray nozzle 33 and shorter than the total sum of the depth of the mounting recess 43 and the depth of the hole 44. Moreover, the dimension from the tip of the spray nozzle 33 of the module 7 to the bottom face of the ring-shaped recess 34 is greater than the total sum of the depth of mounting recess 43 and the depth of hole 44.

On the other hand, the open end wall of the spray nozzle 33 is abutted against the internal wall 47 of the hole 44 to restrict the movement of the spray nozzle 33. Therefore, when the spray nozzle 33 of the spray module 7 is inserted into the bore 42 of the adapter 8 and the spray module 7 and the adapter 8 are pressed against each other, the spray nozzle 33 advances into the spray module 7, with the result that the compressed gas flows though the spray nozzle 33 and bore 42 and is ejected from the side hole 46 of the mounting tip portion 53.

On the other hand, as shown in FIG. 3, the mounting part 2b to which the adapter 8 is attached is formed with the mounting recess 21 in which the mounting tip portion 53 of the adapter 8 is detachably mounted by insertion and the part of the inner wall of this mounting recess which corresponds to the side hole 46 of the adapter 8 is formed with a ring-shaped recess 22 communicable with the gas passageway 23. Furthermore, to insure sealing of the mounting recess 21 with respect to the adapter 8, O-rings 48, 49 are disposed at both sides of the laterally open side hole 46 of the mounting tip portion 53 of the adapter 8, while a cylindrical packing 50 having an annular projection in the circumferential direction is disposed at the tip of the mounting tip portion 53.

The fiberscope and the spray module are used as follows. The spray module 7 is mounted in the mounting recess 43 of the adapter 8, and the module 7 and adapter 8 are pressed against each other, whereupon the compressed gas in the spray module 7 is guided through the spray nozzle 33, the passageway 45 and side hole 46 of the adapter 8 and the gas passageway 23 into the airwater channel 11 and ejected from the end face 9 of the flexible tubular member 3. Therefore, the deposits such as the body fluid etc. deposited at and around the open end of the air-water channel 11 of the flexible tubular member 3 can be removed by a jet of gas. On the other hand, as the pressure applied as above is released, the ejection of compressed gas is terminated or stopped.

Particularly because the part corresponding to the gas orifice of the conventional operator unit is formed with the mounting recess 21 in which the adapter 8 can be mounted and the operator unit 2 of the fiberscope 1 is provided with the adapter 8 for attachment of the spray module 7, the mere procedure of attaching the spray module 7 to the adapter 8 and pressing the spray module 7 relatively against the operator unit 2 results in delivery of compressed gas to the air-water channel 11 of the tubular member 3 and ejection of the gas from the open end (nozzle part) of the channel. Therefore, the deposits such as the body fluid etc. deposited at and around the open end of the air-water channel 11 can be removed with certainty by single-handed operation. Moreover, since the spray module 7 as the compressed gas supply means can be freely connected and disconnected with respect to the mounting portion, the spray module 7 disconnected from the adapter 8 and the fiberscope alone be used for endoscopy and treatment of the digestive organ or the like without being compromised in manipulatability.

Where the removal of deposits by a jet of gas is not necessary, the adapter 8 can be removed from the mounting recess 21 and be set in the mounting recess 21, with the exposed end recess 43 of the adapter 8 being covered with a cap or the like.

Figure 5:
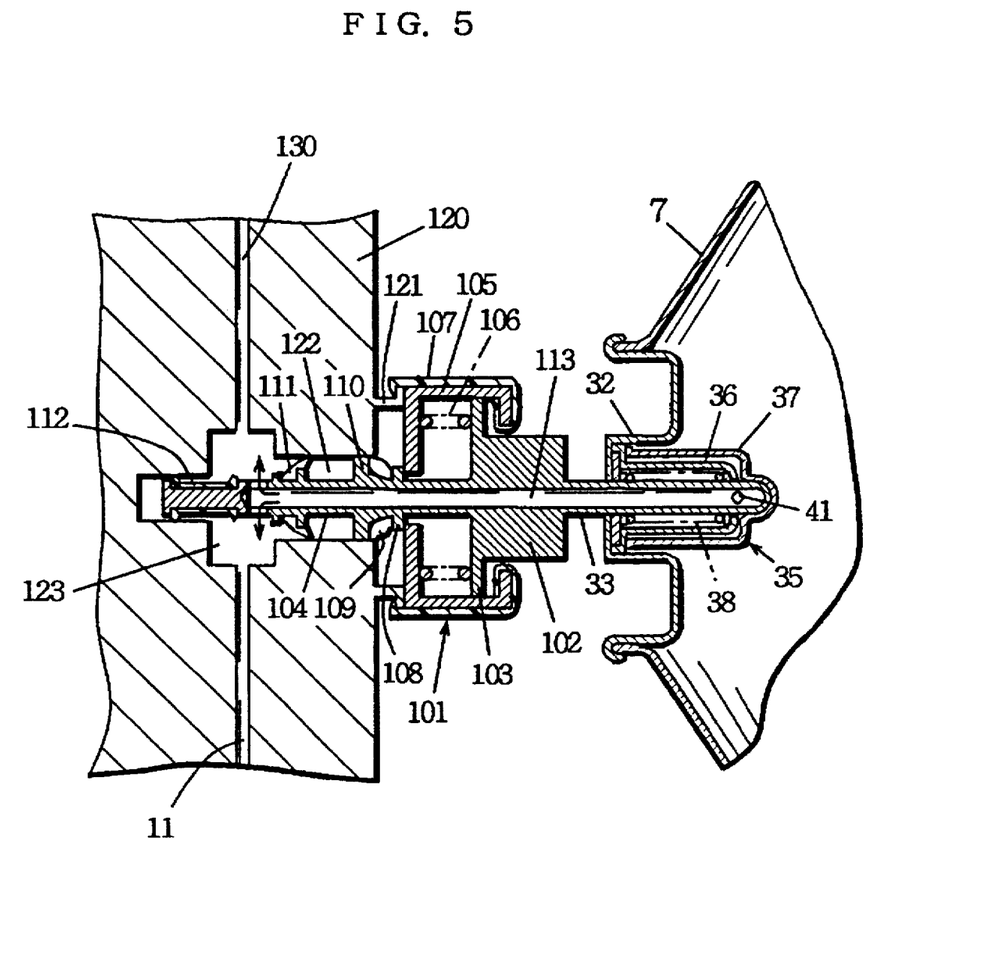
FIG. 5 is a sectional view of another mounting mechanism in the operator means shown in FIG. 1.

FIG. 5 is a cross-section view showing another mounting mechanism of the operator unit. Here, the like numerals are used to indicate the like elements of the above embodiment.

In this embodiment, an adapter 101 is rigidly secured to a spray module 7 of the same construction as that of the embodiment described hereinbefore and this adapter 101 can be mounted in a mounting recess 122 formed at the mounting part 120 of the operator unit.

More particularly, the adapter 101 to be mounted in the mounting part 120 has a button-shaped base portion 102 integral with the spray nozzle 33 of the spray module 7 and a reduced-diameter mounting tip portion 104 extending from the button-shaped base portion in the axial direction of the spray nozzle 33, and the part of the base portion 102 which lies on the side of the mounting tip portion 104 is formed with a flange portion 103. This flange portion 103 is slidably disposed within a casing 105 and restricted in movement toward the spray module 7 by the inside wall of the casing 105. Further disposed in the casing 105 is a spring 106 having a larger preenergizing or biasing force than the coil spring 38 of the spray module 7 for biasing the flange portion 103 externally. Therefore, when the spray module 7 is pressed against the mounting part 120, the valve mechanism of the spray module 7 is opened by the coil spring 38 of spray module 7, whereby the compressed gas is introduced into the spray nozzle 33. As the button-shaped base portion 102 together with the spray module 7 is further pressed toward the casing 105 against the biasing force of the spring 106 of the adapter 101, the mounting tip portion 104 advances into the mounting recess 122 of the mounting part 120.

The mounting tip portion 104 mentioned above is formed with a ring-shaped projection 108 adapted to contact the outer wall of the casing 105 to restrict movement of the casing 105 toward the mounting recess 120 and, as disposed adjacent to this ring-shaped projection, further with an O-ring 109 having an surface inclined toward the casing 105 as well as an annular projection 110 adapted to slidably contact with the mounting recess 120. Furthermore, the part of the mounting tip portion 104 which is outwardly displaced from the annular projection 110 is provided with a flexible packing 111 shaped like a parasol opening toward the spray nozzle 33 and a cylindrical packing 112 is disposed at its tip.

In order that the compressed gas emerging from the spray nozzle 33 may be fed to the air-water channel of the flexible tubular member, a bore 113 communicating with the orifice of the spray nozzle 33 is formed in the axial direction from the button-shaped base portion 102 toward the mounting tip portion 104 and this bore is opened at the side wall between the parasol-shaped flexible packing 111 and cylindrical packing 112 of the mounting tip portion 104.

On the other hand, the mounting portion 120 comprises a projecting ring-shaped member 121 having a collar portion extending from the tip portion laterally outward and the mounting recess 122 formed in an inward region of the ring-shaped member. The collar portion of the ring-shaped member 121 is engageable with the engaging end of a flexible cap 107 capping the casing 105 of adapter 101. In addition, the wall of a mounting recess 122 which corresponds to the opening of the bore 113 of the adapter 101 is formed with a communication space 123 communicating with the air-water channel 11 of the flexible tubular member and the passageway 130 in the air-water supply tube of the light guide unit.

In this adapter 101 and the spray module 7 equipped with the adapter, the bore of the adapter 101 connected to the mounting recess 122 functions in the same way as the bore of the operator unit of the conventional fiberscope. Therefore, by simply connecting the spray module 7 to the bore formed as the mounting recess 122 and forcing it in, without resort to closing up the communication hole, the compressed gas can be ejected from the end of the air-water channel of the flexible tubular member. Moreover, because of the cushioning effect of the spring 106, the compressed gas can be ejected from the end of the air-water channel of the flexible tubular member without applying an excessive pressing force to the spray module 7.

The fluid passageway of the operator means may comprise at least one sub-passageway corresponding to a gas or water supply tube from a gas or water supply means of the light guide unit. Thus, the fluid passageway of the operator means may comprise a gas sub-passageway and a water sub-passageway which are respectively communicable with an air supply tube and a water supply tube extending from a gas supply means and a water supply means of the light guide unit. Further, the air-water channel of the flexible tubular member may comprise an air subchannel and a water subchannel which are communicable with the gas sub-passageway and the water sub-passageway, respectively, and the subchannels may be met or jointed each other on the way of the channel in the tubular member to form the air-water channel extending to a distal end mounted on the tip of the flexible tubular member.

Figure 6:
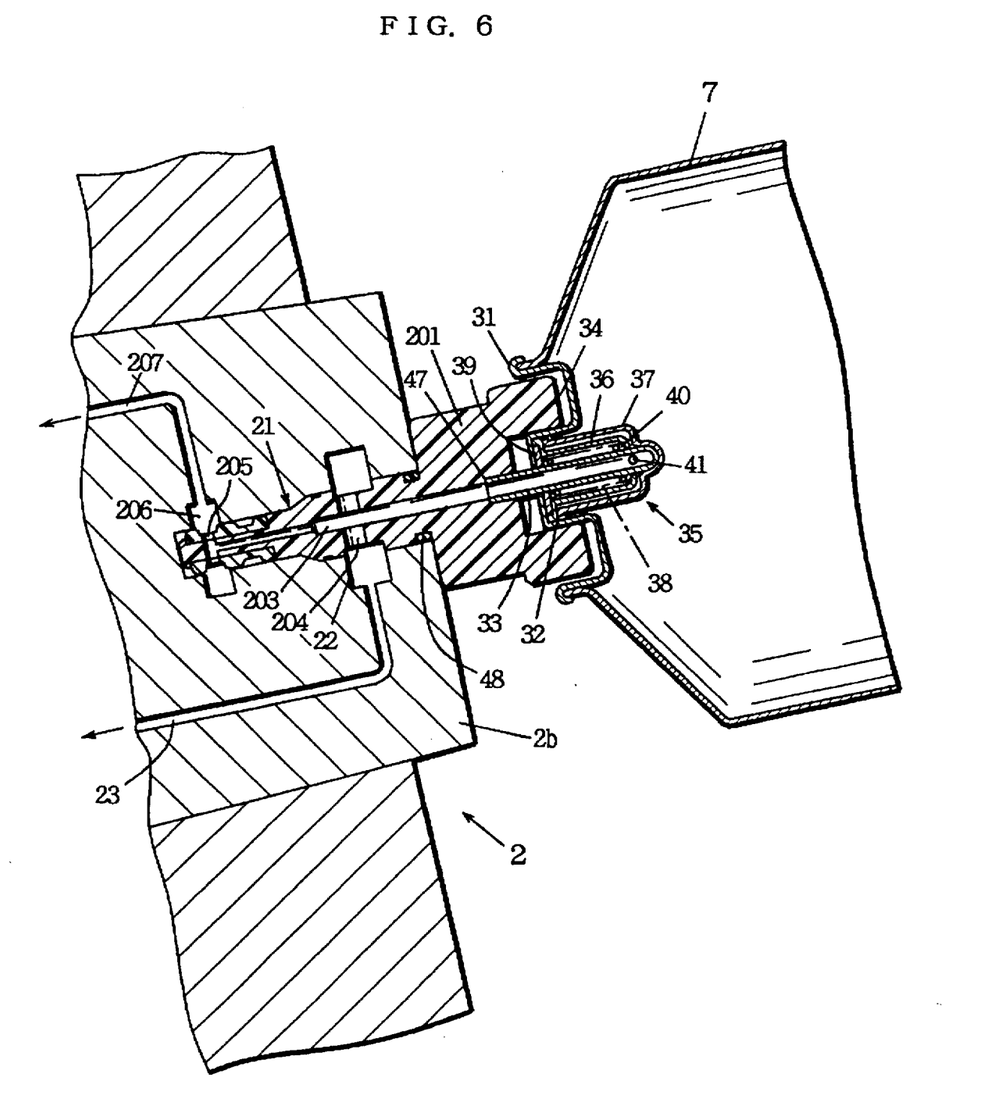
FIG. 6 is a sectional elevation view of a still another mounting mechanism in the operator means shown in FIG. 1.
Figure 7:
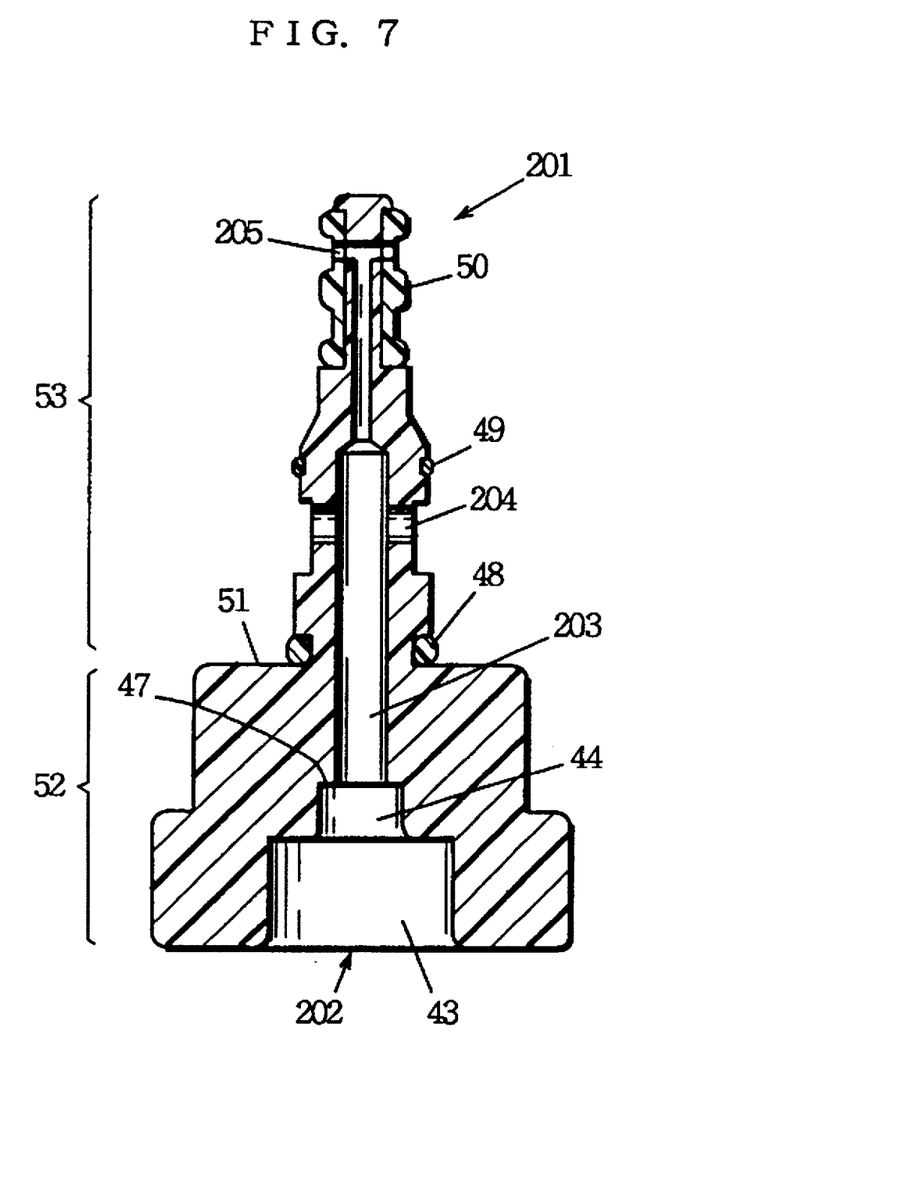
FIG. 7 is a sectional View of the adapter shown in FIG. 6.

FIG. 6 is a sectional elevation view of still another mounting mechanism of the operator means shown in FIG. 1. and FIG. 7 is a sectional view of the adapter shown in FIG. 6. In this embodiment, the adapter 201 has a similar configuration with the adapter 8 shown in FIG. 4 except for a bore configuration. Thus, the bore 202 comprises the cavity 43, the hole segment 44 extending axially from the cavity 43, a passageway 203 extending axially from the hole segment 44, a first side hole 204 extending in both direction perpendicular to the extending direction of the passageway 203 and opening on the way of the passageway at the both side, and a second side hole 205 extending in both direction perpendicular to the extending direction of the passageway 203 and opening at the both side of the tip portion of the adapter 201. The first side hole 204 is communicable with the gas passageway 23 (as a gas sub-passageway through the ring-shaped recess 22 of the operator unit 2, and the second side hole 205 is communicable with a water passageway 207 (as a water sub-passageway) through a ring-shaped recess 206 of the operator unit 2, and the gas passageway 23 and the water passageway 207 respectively reach to a gas subchannel (not shown) and a water subchannel (not shown) formed in the flexible tubular member. Further, the gas subchannel and the water subchannel are met or jointed on the way of the flexible tubular member to form the air-water channel (fluid channel) extending to the open end (nozzle part) of the channel.

Therefore, when the spray module 7 is mounted in the mounting recess 21 of the adapter 201 and the module 7 and the adapter 201 are pressed against each other, the compressed gas in the spray module 7 is guided through the spray nozzle 33, the bore 202 of the adapter 201, the gas passageway 23 and water passageway 207 of the operator unit 2, and the gas subchannel and the water subchannel into the air-water channel of the flexible tubular member 3, and the compressed gas is ejected from the end face of the flexible tubular member 3. Use of the adapter 201 provided with the water passageway 207 in combination with the spray module 7 gives advantages when a lens mounted on the end of the optical fiber of the tubular member is washed with water, particularly hard water. Namely, when an observation or treatment operation with use of the fiberscope, washing operation for washing the lens by supplying water from the water supply means of the light guide unit through the water supply tube, the water passageway 207 of the operator unit 2 and the water subchannel to the air-water channel and hanging operation of the tubular member for dripping out the fluid spontaneously are conducted repeatedly, the scale due to water is deposited and accumulated on the open end of the air-water channel of the flexible member of the fiberscope. According to the present invention, not only the deposits due to the body fluid but also the deposited scale due to water can be efficiently removed from the tip of the flexible tubular member 3 by the ejected jet gas.

In the fiberscope of this invention, the compressed gas supply means need only be a device capable of supplying a compressed gas and, therefore, is not limited to the spray module described above but may be any pressure-resistant container (such as a bomb) provided with an opening-closure means such as a check valve or cock, or a compressor, among others.

The mounting means for connecting the compressed gas supply means need only be a device that is capable of detachable connection of the compressed gas supply means and, as such, is not limited to the adapter described hereinbefore but can be liberally selected according to the type of compressed gas supply means. Taking a pressure-resistant container provided with an opening-closure means as an example, all that is necessary is that the connecting end such as the nozzle or hose of the pressure-resistant container can be appropriately connected. In the case of a compressor, what is necessary is that the connecting end of a hose leading from the compressor can be accepted to establish the necessary communication.

The mounting means comprises an adapter that can be connected to the connecting end of the compressed gas supply means and a mounting part (mounting recess) formed in the operator means and capable of accepting the adapter. In case the compressed gas supply means is a spray module or container which is simple in operation and superior in portability, the use of the adapter enables positive cleaning and prevention of plugging of the end opening of the channel with jets of gas by a simple operation of mounting and pressing-in.

The adapter need only be located in an intermediate position between the compressed gas supply means and the operator means and may be detachably mounted or secured to whichever desired of the operator means and the compressed gas supply means. For example, the adapter may be rigidly secured to the mounting part of the operator unit to constitute a mounting portion and the compressed gas supply means be detachably connected to the adapter. Conversely, the adapter may be secured to the compressed gas supply means and the adapter be detachably connected to the mounting part (mounting recess) of the operator unit. Furthermore, in the embodiment illustrated in FIG. 5, where the spray nozzle 33 and the adapter 101 form an integral unit, the base portion 102 of the adapter 101 may be formed with a mounting recess complementary to the tip of the spray nozzle 33 and the tip of the spray nozzle 33 may be detachably mounted in the mounting recess.

Though, in the above embodiment, the adapter is formed with a bore communicable with the compressed gas supply means, the aperture of the bore need not be located on the side of the adapter but may be located at the tip portion of the adapter only if it is communicable with the compressed gas supply means. Moreover, all that is necessary is that the operator unit is formed with a gas passageway communicable with the bore of the adapter and the air-water channel of the tubular member and, like the communication space 123 illustrated in FIG. 5, this gas passageway may constitute a part of the air-water channel 11 of the flexible tubular member 3 and/or the gas-water passageway of the light guide 4.

Furthermore, whereas in the above embodiment, the mounting part or site (mounting recess) for mounting the adapter is situated in the region corresponding to the bore of the conventional operator unit, the mounting part may be located in any appropriate position of the operator unit, such as in the grip portion 2a.

Where the compressed gas supply means is a spray module, the mounting means is preferably provided with a control or regulating means which precludes or obstructs the movement of the spray nozzle in an axially outward direction and driving the spray nozzle deeper into the pressure-resistant container in association with application of a pressing force. Whereas, in the above embodiment, the control means comprises the internal wall 47 capable of plane contact with the end face of the spray nozzle, the control means may for example comprise an engaging portion engageable with a concave/convex portion formed at the side of the shaft portion of the spray nozzle, provided only that it successfully delimits the axially outward movement of the spray nozzle.

Further, whereas the gas-water supply line of the adapter is provided with a check valve (control means) in the foregoing embodiment to prevent the gas from the compressed gas supply means from being ejected from the gas-water supply tube of the light guide unit, such control means may be provided in the line from the passageway in the gas-water supply tube to the bore of the adapter.

It is essential and sufficient that the spray module of this invention comprises a pressure-resistant container filled with a compressed gas, a spray nozzle which is capable of advancing deeper into the pressure-resistant container, a valve mechanism by which the compressed gas is delivered from the spray nozzle, and an adapter connectable to the operator unit for the flexible tubular member of the fiberscope. The valve mechanism mentioned above is not limited to the mechanism described in the foregoing embodiment but may be such that the compressed gas in the pressure-resistant container may be ejected from the spray nozzle in association with the inward movement of the nozzle into the container. Moreover, the adapter may be rigidly secured to the spray nozzle or detachably connected to the spray nozzle and/or the spray module. As mentioned hereinbefore, the adapter is formed with a bore for communicating the spray nozzle with the channel of the flexible tubular member through the fluid passageway formed in the operator unit.

What is claimed is:

1. A spray module for a fiberscope comprising an elongated flexible tubular member having (i) an axially extending channel and (ii) an operator means connected to said tubular member for executing an endoseopic observation and/or operation through said channel, formed with a fluid passageway communicated with said channel and having a mounting means for detachably connecting a compressed gas supply means for feeding a compressed gas to said channel through said fluid passageway, which comprises a pressure-resistant container filled with a pressurized gas, a spray nozzle capable of advancing inwardly with respect to said pressure-resistant container, a valve mechanism for ejecting the compressed gas in said pressure-resistant container from said spray nozzle in association with the inward displacement of the spray nozzle, and an adapter which can be connected to an operator means, said adapter being provided with a bore for communicating said spray nozzle with the channel of the tubular member through a fluid passageway formed in an operator means.

2. The spray module according to claim 1, wherein the adapter is detachably mounted on the spray nozzle.

3. The spray module according to claim 1, wherein the adapter can be connected to a mounting part of the operator means.

4. The spray module according to claim 3, wherein the mounting part comprises a mounting recess formed in the operator means and adapted to accept the adapter.

5. The spray module according to claim 1, wherein the adapter is provided with a control means which precludes the movement of the spray nozzle in an axially outward direction and driving said spray nozzle inwardly with respect to the pressure-resistant container in association with the application of a pressing force.

6. The spray module according to claim 1, wherein the valve mechanism comprises a first cylindrical valve member having a collar at one end and a throughhole at the other end for the spray nozzle, a second cylindrical valve member housing said first cylindrical valve member in an axially reciprocable manner and adapted to lock or support the spray nozzle extending through the first cylindrical valve member at the bottom thereof, a sealing means for sealing the part between said first spray nozzle and the spray nozzle at the both ends of said first cylindrical valve member, and a first spring disposed between said first cylindrical valve member and said second cylindrical valve member for biasing the spray nozzle axially outwardly.

7. The spray module according to claim 6, wherein the adapter is secured to the outer end of the spray nozzle and comprises a base integral with said spray nozzle and having a flange, a casing accommodating slidably said flange and having an inside wall for restricting the movement of said flange inwardly with respect to said spray nozzle, and a second spring disposed in said casing and having a larger biasing force than the first spring for biasing said flange outwardly.

8. The spray module according to claim 1, wherein said channel of the tubular member comprises a gas-sub-channel and a water-subchannel which are met or jointed each other on the way of the channel to form the channel extending to an open end of the tubular member, and said fluid passageway comprises a gas sub-passageway which is communicable with a gas supply tube extending from a light guide unit and the gas subchannel of the channel, and a water sub-passageway which is communicable with a water supply tube extending from the light guide unit and a water sub-channel of the channel.

9. A fiberscope comprising an elongated flexible tubular member having an axially extending channel and an operator means connected to said tubular member for executing an endoscopic observation and/or operation through said channel and having a mounting means for detachably connecting a compressed gas supply means for feeding a compressed gas to said channel, wherein said mounting means comprises an adapter which can be mounted on said compressed gas supply means and a mounting recess of said operator means which is adapted to accept said adapter, said adapter being formed with a bore communicable with said compressed gas supply means, and said operator means being formed with a fluid passageway communicable with said bore of the adapter and said channel of the tubular member.

10. The fiberscope of claim 9, which has a mounting recess to which said adapter is and a compressed gas supply means which can be connected and disconnected with respect to said adapter.

11. The fiberscope of claim 9, which is provided with a mounting recess formed in said operator means and a compressed gas supply means to which the adapter capable of being mounted in said mounting recess is secured.

12. The fiberscope of claim 9, wherein said compressed gas supply means is a spray module filled with a pressurized gas.

13. The fiberscope of claim 9, wherein said compressed gas supply means is a spray module comprising a pressure-resistant container filled with a pressurized gas, a spray nozzle which is inwardly displaceable with respect to said pressure-resistant container, and a valve mechanism for ejecting the compressed gas in said pressure-resistant container from said spray nozzle in association with the inward displacement of said spray nozzle and said mounting means is provided with a control means for restricting the axially outward movement of said spray nozzle and driving the spray nozzle inwardly with respect to the pressure-resistant module in association with the application of a pressing force.

14. The fiberscope of claim 9, which comprises an elongated flexible tubular member having an axially extending air-water channel, an operator means connected to said tubular member and having a mounting means to which the spray nozzle of said spray module can be connected, and an air-water line extending from said operator means and communicating with said air-water channel, said mounting means comprises an adapter which can be connected to said spray nozzle and a mounting recess formed in said operator means and adapted to accept said adapter, said adapter is formed with a bore communicable with said spray nozzle, said operator means is formed with a fluid passageway communicable with the bore of said adapter and the air-water channel in said tubular member, and a control means is interposed in the passageway from said air-water line to the bore of said adapter for controlling or obstructing the inflow of the fluid ejected from said spray nozzle into said air-water line.

15. A method of cleaning or removing deposits at an open end of a channel of a tubular member of a fiberscope using the spray module as claimed in claim 1, which comprises ejecting a compressed gas from the spray nozzle of said spray module to the open end of the channel axially extending in the elongated flexible tubular member of the fiberscope.

* * * * *